United States Patent [19]
Koopman

[11] Patent Number: 5,620,474
[45] Date of Patent: Apr. 15, 1997

[54] SYSTEM AND METHOD FOR DETERMINING INDICATED PACEMAKER REPLACEMENT TIME BASED UPON BATTERY IMPEDANCE MEASUREMENT

[75] Inventor: Jan Koopman, Dieren, Netherlands

[73] Assignee: Vitatron Medical, B.V., Dieren, Netherlands

[21] Appl. No.: 427,418

[22] Filed: Apr. 24, 1995

[51] Int. Cl.$^6$ ............................................. A61N 1/37
[52] U.S. Cl. .................................................. 607/29
[58] Field of Search ............................ 607/27–29, 32, 607/34; 324/430

[56] References Cited

U.S. PATENT DOCUMENTS

| | | | |
|---|---|---|---|
| 4,245,643 | 1/1981 | Benzing, III et al. | 607/28 |
| 4,259,639 | 3/1981 | Renirie et al. | 324/430 |
| 4,437,466 | 3/1984 | Saulson et al. | 607/34 |
| 4,556,061 | 12/1985 | Barreras et al. | |
| 4,715,381 | 12/1987 | Moberg. | |
| 4,899,750 | 2/1990 | Eckwall | 607/28 |
| 5,137,020 | 8/1992 | Wayne et al. | |
| 5,193,538 | 3/1993 | Eckwall | 607/28 |
| 5,247,930 | 9/1993 | Begemann et al. | 607/11 |
| 5,350,411 | 9/1994 | Ryan et al. | 607/32 |
| 5,391,193 | 2/1995 | Thompson | 607/29 |
| 5,458,624 | 10/1995 | Renirie et al. | 607/29 |

FOREIGN PATENT DOCUMENTS

0058603  8/1982  European Pat. Off. ............. 607/29

Primary Examiner—Jeffrey R. Jastrzab
Attorney, Agent, or Firm—Woodcock Washburn Kurtz Mackiewicz & Norris

[57] ABSTRACT

A programmable pacing system and method, the system having the capability for providing an indication of recommended replacement time (RRT) as well as a prior warning of six months to RRT. RRT is determined by storing a value in the pacemaker corresponding to battery impedance at RRT, continuously periodically measuring battery impedance, and comparing the measured value with the stored RRT value. Whenever the pacemaker is reprogrammed to different operating conditions which affect RRT, or there is a significant change in load lead resistance, a new value of RRT impedance is calculated based upon a selected formula corresponding to the reprogrammed set of operating conditions, and stored in the pacemaker. At the same time, an Aging value of impedance is re-calculated to provide a six month warning before RRT, and likewise stored in the pacemaker.

17 Claims, 4 Drawing Sheets

SYSTEM AND METHOD FOR DETERMINING INDICATED PACEMAKER REPLACEMENT TIME BASED UPON BATTERY IMPEDANCE MEASUREMENT

BACKGROUND OF THE INVENTION

The present invention relates to cardiac pacemaker systems and, in particular to such systems having the capability of indicating when the implanted pacemaker should be replaced due to battery depletion.

Implantable cardiac pacemakers are powered by batteries that have an initial energy capacity, which is a first and primary determinant of effective pacemaker lifetime. For example, lithium iodide batteries used in implantable pacemakers manufactured by Vitatron Medical, B.V., the assignee of this invention, have capacities varying from 600 mAh up to 1800 mAh. Starting with the battery capacity at beginning of life (BOL), the anticipated duration to effective end of life (EOL) is also a function of the operating conditions, e.g., the parameters of the pace pulses being delivered and the effective output load, or lead resistance. It is, of course, important to know when the battery is almost depleted, or empty, in order to safely replace the implanted pacemaker. As is known, an implantable pacemaker does not provide the ability to replace only the battery, which is sealed within, but rather the entire pacemaker must be replaced. Thus, it has been a longstanding concern of the pacemaker industry to provide an accurate indication of the battery status, and an accurate prediction of when the pacemaker is going to need to be replaced.

A number of techniques have been used in pacemakers for determining the status of the battery and indicating when the pacemaker is essentially at EOL and needs to be replaced. For example, it is known in the prior art to measure the battery impedance, which is well known for various lithium iodide battery models. The characteristic of battery impedance as a function of energy used, i.e., depletion level, is available in all cases, and is an accurate indication of energy used, and consequently of remaining available energy. However, the predictive value of the impedance measurement depends upon knowing the actual functioning conditions, i.e., ongoing current consumption. Thus, while an accurate impedance measurement can indicate the remaining energy, the remaining useful time is dependent upon operating conditions.

Another approach, which may be used alone or in combination with the impedance measurement, is that of a hardware comparator which compares the battery voltage with a reference voltage set to represent the voltage at which EOL is declared. Such a subsystem is substantially completely hardware driven, which has certain advantages. The battery voltage measurement also has an accuracy advantage, since it measures the actual operating parameter which defines when the pacemaker is operating within tolerance. Such a system guards that if the output voltage drops below the reference level corresponding to recommended replacement time (RRT), a flag is set, and the pacemaker can be automatically switched to a less energy-consuming mode of operation. However, the voltage measurement system is not so accurate a predictor of when RRT will come, meaning that the physician does not get an early warning of when to bring the patient back for pacemaker replacement.

Another prior art approach is that represented by U.S. patent application Ser. No. 08/132,713, filed Oct. 6, 1993, now U.S. Pat. No. 5,458,624 and assigned to the same assignee as this invention. The approach of this system is to provide a circuit for constantly obtaining a measure of the total battery current expenditure to determine battery depletion, rather than measuring battery parameters. Based upon a determination of what percentage of the battery capacity has been expended, and using the current rate of energy consumption, the physician can then project an effective lifetime for the pacemaker. This basic concept of projecting EOL by accumulating a measure of energy usage in an implanted pacemaker is also illustrated in U.S. Pat. Nos. 4,556,061 and 4,715,381. Such systems in practice require significant additional hardware and software in order to achieve their accuracy.

So long as the impedance measuring system can reliably provide sufficient advanced warning, it remains a recommended system due to its good predictability and its relative simplicity. While a voltage measurement system characterizes the present state of the battery within its functioning mode, and thus can signal actual RRT with a high accuracy, the overriding need of the physician is accurate predictability of when the implanted pacemaker needs to be replaced. These considerations indicate that a simple impedance measurement system is an optimal design choice if it can be adapted to account for changed current consumption conditions. However, since the predictability is a function of ongoing current consumption, the impedance measurement system must be supplemented by a capability to adapt the RRT determination in accordance with changed pacing conditions.

In the design of the system of this invention, we define three points in time which present important requirements which must be met. These requirements are defined in terms of tolerated drop of the programmed value of the output pulse. At RRT, the recommended replacement time, the output voltage must be greater than 80% of the programmed value. At last replacement time (LRT), the output voltage must still be at least 60% of the programmed value. Further, the time period between RRT and LRT, where the pacemaker is operating at standard conditions, e.g., 4.0 volts, must be three months for 99.7% of the population (3 sigma). The "Aging time" is defined as that time where, at standard conditions, the pacemaker has at least 6 months remaining until RRT, for 99.7% of the population (3 sigma). By providing an indication of Aging time, the physician can plan for a patient visit safely ahead of LRT, and can minimize RRT operation. These times are exemplary for purposes of this preferred embodiment, and it is to be understood that they can be defined differently.

By using battery tables available, the battery impedance value for RRT and Aging, can be determined for standard pacemaker operating conditions. This invention further provides means for adapting determination of RRT and Aging when any other pacing condition is programmed.

SUMMARY OF THE INVENTION

The present invention provides a simple and accurate system and method for determining pacemaker replacement time based upon measurements of a battery parameter, preferably battery impedance, which changes with battery depletion. The system and method are adaptable to take into account any change, programmed or automatic, in pacemaker operating conditions. The maximum allowed battery impedance for an initially programmed set of operating conditions is determined based upon battery characteristics, and stored in the pacemaker as a reference, preferably in RAM. The pacemaker periodically measures battery impedance compares it with the reference value, and sets an RRT flag if the measured battery impedance is higher than the stored reference value. In one preferred embodiment of this invention, an external programmer which communicates with the pacemaker contains stored adjustment factors corresponding to other programmable pacing conditions and values of lead impedance. Whenever pacing conditions are changed by the programmer (e.g., voltage or pulse duration), or a new value of lead impedance is determined, the appropriate factor or factors are selected and used to recalculate the RRT impedance. The new RRT value is stored as the reference value in the pacemaker RAM, and used to trigger RRT mode when battery impedance increases to the RRT value. A new value of impedance corresponding to the aging time is likewise recalculated by a stored factor, and used to signal "Aging." Thus, any time the pacemaker operating conditions are reprogrammed, the Aging and RRT values of impedance are recalculated, so that the prediction of these values is accurately adapted to the new pacing conditions. When and as the physician obtains an indication that battery impedance has risen above the Aging level, the physician is able to plan for pacemaker replacement. At the time that RRT is reached, the pacemaker automatically places the pacemaker into a VVI mode of operation, where the pacemaker can function within specifications due to a lower current consumption.

In a preferred embodiment, the system recognizes a plurality of specific operating conditions, each of which is associated with a respective factor for changing values of RRT and Aging. Changes to predetermined values of pulse voltage, pulse duration, and lead impedance are changes to which the system responds by applying an adaptive factor or factors; other operating parameters of lesser influence on current consumption can also be employed within the scope of the invention.

Although the current preferred embodiment of the invention utilizes an external programmer to recalculate values of RRT corresponding to programmed changes, or monitored changes in lead impedance, in another embodiment of this invention these changes are made automatically by the implanted pacemaker in response to automatic determination of change in lead impedance or automatic switching of pacing operation.

DESCRIPTION OF THE PREFERRED EMBODIMENTS

DESCRIPTION OF THE PREFERRED EMBODIMENTS

In the preferred embodiment of this invention, impedance measurement alone is used to determine RRT. The impedance measurement is discussed below in connection with FIGS. 2 and 3. Based upon battery characteristics and pacemaker current consumption at standard operating conditions, a value of battery impedance is initially determined as corresponding to RRT. This impedance value, referred to as RRT impedance, is that battery impedance at which RRT would occur, given the maintenance of the same pacemaker operating conditions until RRT. Stated alternatively, the RRT impedance correlates to the battery condition when a predetermined battery life remains, and it is desired to replace the pacemaker. The pacemaker begins life operating under standard conditions, and with this initial value of RRT impedance stored in its memory. The pacemaker continually measures battery impedance ($R_o$), which increases with time and energy depletion (FIG. 3), and determines when it reaches the RRT impedance. When and as the pacemaker is programmed to significantly different operating conditions, the RRT impedance is recalculated to reflect the changed rate of battery energy depletion. For example, programming the output pulse to a significantly greater voltage level results in greater current flow and a greater rate of battery depletion. The pacemaker of this invention reacts by calculating a lower RRT impedance, meaning that RRT is reached earlier in the pacemaker lifetime.

The system and method of this invention are described in the environment of a representative pacemaker having exemplary characteristics. The invention has been designed to operate in such a pacemaker having a longevity of 5.42 years for 50% of all units, at standard pacing mode. This figure is exemplary only and will, of course, be different for different pacemaker models. This exemplary pacemaker uses a Zeta 203 battery, and has a standard capacity of about 1088 mAh. Longevity is calculated based upon requirements that the pacemaker have 3-months lifetime between RRT and LRT for 95% (2*sigma) of the population; 6-months lifetime between Aging and RRT for 95% (2*sigma) of the population; a communication distance between the pacemaker and the programmer at RRT and LRT greater than 3 cm; at LRT, during special communications in the standard pacing mode, the output voltage must be greater than 60% of the program value; at RRT during special communications in the standard pacing mode, the output voltage must be greater than 80% of the program value; and during special communications in other modes than the standard pacing mode, the output voltage must be greater than 70% of the programmed value.

An analysis of a pacemaker defined by the above environment provides an empirical indication of which parameters have a significant influence on the RRT point, i.e., the battery impedance corresponding to recommended replacement time. Rate has been considered, but because rate may change constantly, i.e., in a rate responsive mode, this would mean that the RRT impedance value would have to be recalculated constantly. This would not be advisable, particularly for a patient known to have repeated episodes of starting and stopping exercise. For an embodiment where the RRT determination is done automatically in an implanted pacemaker, average rate may be calculated over a relatively long period of time, e.g., weeks, and adjustments made to the RRT point at corresponding time intervals. For the preferred embodiment of this invention, the RRT impedance value is changed only with a programmer; while a programmed change in rate could be used, because of its relatively small influence, rate is not a parameter utilized for recalculating the RRT impedance.

Lead impedance is determined during an autoread status operation, and is observed to have a large influence on the current consumption of the pacemaker. Accordingly, this parameter is used to calculate a new RRT impedance value, when appropriate. Likewise, pulse width has a large influence on pacemaker current consumption, since the pulse width is known by the programmer, this parameter is used by the programmer to calculate a new RRT impedance value when appropriate. Similarly, output voltage, also known by the programmer, has a significant influence on current consumption, and is used when appropriate to calculate a new RRT impedance value.

The mode of operation has relatively small influence on current consumption, and accordingly, changes in mode as such are not used to recalculate RRT impedance value. It is to be noted, however, that this is a compromise judgement, and a recalculation factor attributable to mode changes can be used within the scope of this invention. Likewise, any other parameter which, when changed, has any influence on ongoing current consumption, can be factored into a recalculation of RRT load impedance.

Figure 1A:
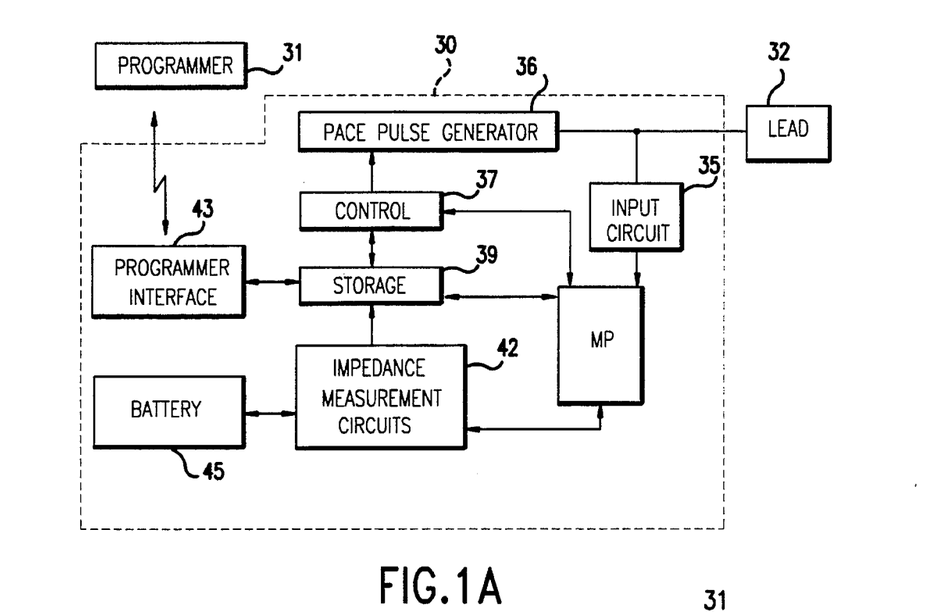
FIG. 1A is a block diagram showing the primary functional components of a pacing system of the preferred embodiment of this invention.

Referring now to FIG. 1A, there is shown a block diagram of the primary functional components of the system of a preferred embodiment of this invention. The preferred embodiment illustrated comprises an implantable pacemaker 30, an external programmer 31, and a lead 32 for delivering signals between the pacemaker and the patient's heart. The components of the pacemaker illustrated in this figure are only those pertinent to carrying out the subject invention, and it is understood that a functioning implantable pacemaker has a great many different components, as well as stored software, which are not illustrated. See, for example, U.S. Pat. Nos. 5,247,930 and 5,350,411, incorporated herein by reference, illustrating in more detail the primary components of an exemplary implantable pacemaker.

The pace pulse generator 36 delivers pace pulses, under influence of control circuitry 37, for delivery through lead 32 to the patient's heart. Control 37 controls pace pulse parameters such as output voltage and pulse duration; in the exemplary embodiment of this invention, output voltage settings are 1.3, 2.7, 4.0, 5.3 and 8.0 volts, and pulse widths can be programmed in 25 microsecond steps, within a range of 0.1 ms to 1.0 ms. Control circuitry 37 acts under the influence of microprocessor 38 and information from storage 39. Storage 39 may suitably be RAM storage associated with the microprocessor subsystem. Detected signals from the patient's heart are processed in Input circuit 35, and forwarded to microprocessor 38 for use in logic and timing determination, in a known manner. Programmer 31 communicates with programmer interface block 43, to obtain data which is transferred to storage 39, for use in changing pacing conditions, and undertaking tasks such as impedance measurement. The programmer is used to initiate a lead impedance measurement, which is a standard pacemaker system operation. The lead impedance measurement is carried out by a first of the circuits illustrated in block 42, under control of microprocessor 38.

The implantable pacemaker is powered by a battery 45, which supplies electrical power to all of the electrically active components of the pacemaker. Block 42 also contains an impedance measurement circuit, described in more detail in connection with FIG. 2, which measures the battery impedance automatically on a periodic basis, under control of microprocessor 38.

Figure 1B:
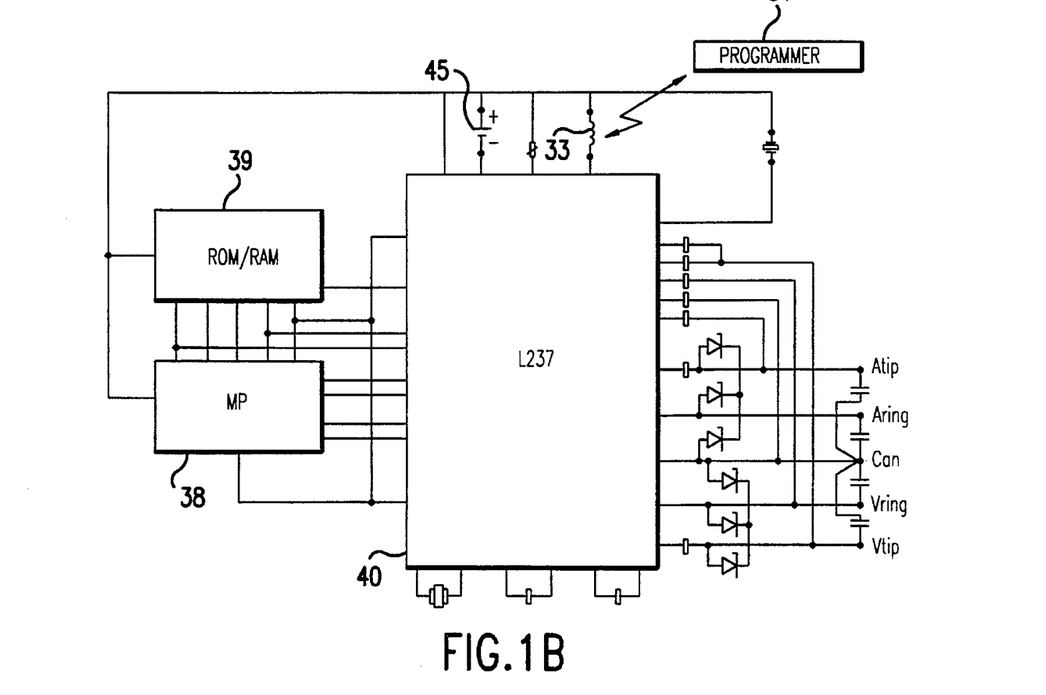
FIG. 1B is a block diagram showing the relationship of pacemaker's microprocessor, ROM/RAM memory, and a clip which carries out timing and control functions under control of the microprocessor.

Referring now to FIG. 1B, there is shown a block circuit diagram of the pacemaker of this invention. A chip 40, designated L237, holds circuitry for performing control and timing functions, and includes the following components:

power supply
voltmeter (DVM)
transceiver
activity sensor processor
crystal oscillator and timer
amplifiers—for signals received from patient
modem
output timing logic
watchdog and back-up pacer
bus unit and address decoders
high-rate protection circuit
output voltage generator
output driver Chip 40 is interconnected with ROM/RAM storage 39, and microprocessor 38, as shown. A coil 33 receives transmissions from programmer 31. A battery 45 provides power to all components. Outputs are indicated for a dual chamber pacer, with connections through lead 32 to atrial electrodes designated $A_{tip}$ and $A_{ring}$; ventricular electrodes designated $V_{tip}$ and $V_{ring}$; and to the pacemaker can, system neutral.

Figure 2:
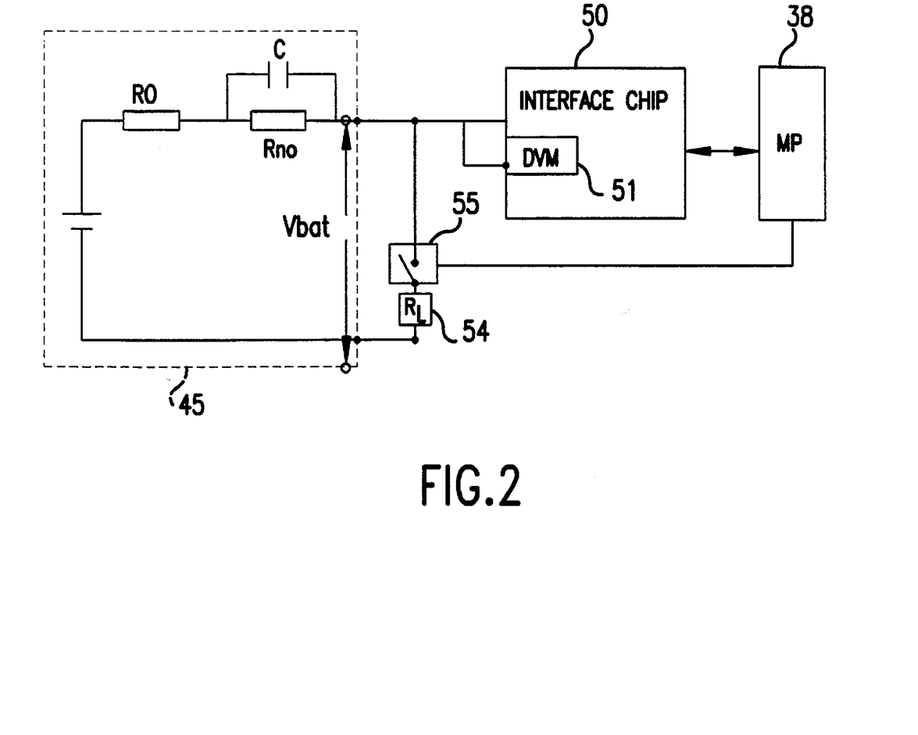
FIG. 2 is a circuit diagram of the primary components utilized for impedance measurement in a preferred embodiment of this invention.
Figure 3:
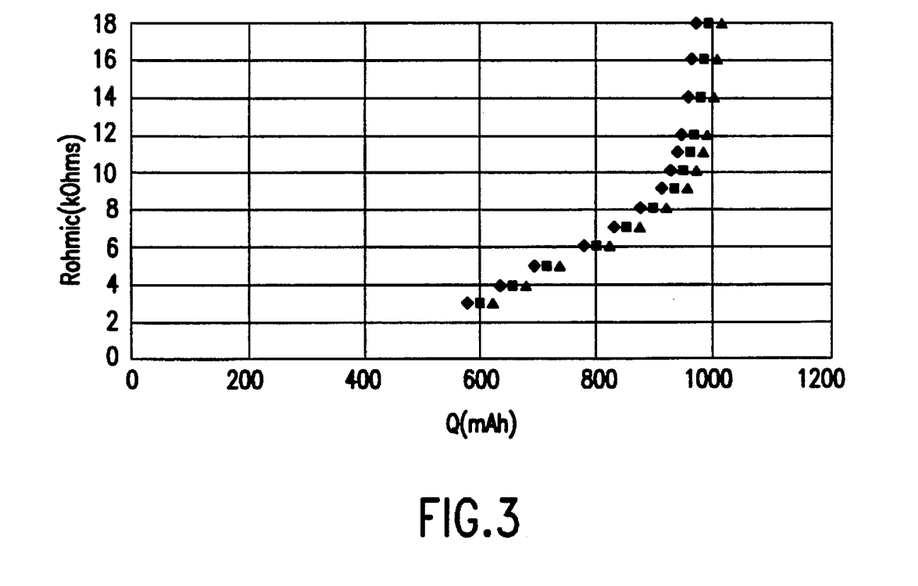
FIG. 3 is a graph showing the variation of battery ohmic resistance as a function of battery energy expenditure.

Referring now to FIG. 2, there is shown a circuit diagram which includes a model of the battery 45, shown as an ideal voltage source and impedance elements. The battery output is shown connected to a digital voltage measurement unit 51, which is used by the pacemaker for making battery impedance measurements, as discussed in more detail below. As shown in the model of the battery, it is represented by an ideal voltage source, a series resistor $R_o$ and a parallel combination made up of $R_{no}$ and C. The $R_o$ value, also referred to as $R_{ohmic}$ is the impedance value used as a measure for obtaining RRT. Referring to FIG. 3, there is shown a graph of the variation of $R_{ohmic}$ in Kilohms, versus battery energy expended, i.e., Q (mAh). The statistical variations of this curve for the battery type as specified above, indicate that impedance measurement is a good predictor of the amount of energy still available inside the battery, i.e., the error in estimating remaining service time is within an acceptable range. As set forth above, this predictability feature enables the choice of a single impedance measurement subsystem for determining battery EOL, or RRT.

From FIG. 3, it can also be seen how RRT is determined. Given a value of $R_{ohmic}$, one can determine the difference between a programmed pulse voltage level and actual delivered voltage level, for standard conditions. Thus, a value of $R_o$ can be found that meets the above RRT criteria. Also, since it must be three months from RRT to LRT, the incremented mAh over three months can be used to find a value of $R_o$ corresponding to an additional three months depletion. The RRT impedance is determined as the highest value of $R_o$ where the criteria for both RRT and LRT are met, and there is at least a three months lapse between RRT and LRT. The value of $R_o$ for Aging is then determined as a value which gives at least six months lifetime until RRT.

Referring again to FIG. 2, there is shown connected to the battery output an interface chip 50, which contains a Digital Voltage Measurement (DVM) unit 51. Chip 50 and DVM 51 are connected to microprocessor 38. Microprocessor 38 also controls switch 55 which, when closed, connects a resistor 54 designated $R_{load}$ across the battery output for a short duration. The DVM unit uses a dual slope analog to digital conversion technique, which provides a measurement in counts. The battery impedance, or "delta count" from the DVM, is measured when the battery is loaded with $R_1$ and unloaded, under control of microprocessor 38. From these two measurements the battery impedance $R_o$ is measured using the formula:

$$R_o = R_{load} * (U_{unloaded}/U_{loaded} - 1)$$

In the preferred embodiment, battery impedance is measured every 24 hours, e.g., every midnight. Other intervals can be used, so long as there is a continued type of measurement. The result in delta count is compared with the stored delta counts already stored in RAM, which indicate the Aging and RRT values. When and as the measured delta count is higher than either one of these values, the corresponding Aging or RRT flag is set, and the pacemaker changes rate automatically. As stated above, when the RRT flag is set, the pacemaker also is switched to VVI mode, to ensure that it operates within specifications during the remaining lifetime until LRT.

For the exemplary battery described, Zeta 203, we have compiled figures giving the variation, or tolerance in output voltages from the programmed value, at different conditions. These are set forth in Table 1 below, wherein $U_o$ is the programmed pulse output in volts; $R_1$ is the lead resistance in ohms; $T_p$ is the pulse width, or duration in ms; $I_{bat}$ is the expended battery current; $U_{o-1}$ is the minimal relative output amplitude during a read status; and $U_{o-2}$ is minimal relative output amplitude. The "Impedance Measurement" figures correspond to chosen mAh and $R_o$ values at uncorrected RRT, i.e., RRT determined on the premise of standard conditions ($V_o$=4.0 V; $R_l$=500 ohms; $T_p$=0.4 ms). However, since significantly greater current is drawn at 8 volts, lower RRT values are chosen for all 8.0 volt combinations.

TABLE 1

| Condition: DDD | | | | | Impedance measurement | | | | |
|---|---|---|---|---|---|---|---|---|---|
| $U_o$ V | $R_f$ Ω | $T_P$ ms | rate ppm | Ibat μA | Q mAh | $R_o$ kΩ | $R_{no}$ kΩ | $U_o$1 % | $U_o$2 % |
| 1.3 | 2000 | 0.1 | 40 | 8.4 | 910 | 8908 | 6754 | 92 | 102 |
| 1.3 | 2000 | 0.1 | 60 | 9.7 | 910 | 8908 | 6754 | 92 | 102 |
| 1.3 | 500 | 0.4 | 60 | 11.5 | 910 | 8908 | 6754 | 85 | 94 |
| 1.3 | 200 | 1.0 | 60 | 12.6 | 910 | 8908 | 6754 | 78 | 88 |
| 2.7 | 2000 | 0.1 | 60 | 9.9 | 910 | 8908 | 6754 | 87 | 92 |
| 2.7 | 500 | 0.4 | 60 | 12.5 | 910 | 8908 | 6754 | 82 | 91 |
| 2.7 | 200 | 1.0 | 60 | 22.5 | 910 | 8908 | 6754 | 70 | 83 |
| 4.0 | 2000 | 0.1 | 60 | 10.6 | 910 | 8908 | 6754 | 88 | 98 |
| 4.0 | 500 | 0.4 | 60 | 18.5 | 910 | 8908 | 6754 | 80 | 91 |
| 4.0 | 200 | 1.0 | 60 | 38.0 | 937 | 8908 | 4680 | 47 | 79 |
| 5.3 | 2000 | 0.1 | 60 | 11.2 | 910 | 8908 | 6754 | 89 | 98 |
| 5.3 | 500 | 0.4 | 60 | 25.0 | 910 | 8908 | 6754 | 74 | 88 |
| 5.3 | 200 | 1.0 | 60 | 61.0 | 937 | 8908 | 4680 | 26 | 67 |
| 8.0 | 2000 | 0.1 | 60 | 13.5 | 758 | 5492 | 4484 | 92 | 99 |
| 8.0 | 500 | 0.4 | 60 | 47.0 | 825 | 5492 | 3048 | 79 | 88 |
| 8.0 | 200 | 1.0 | 60 | 112 | 811 | 5492 | 2850 | 26 | 52 |
| 8.0 | 200 | 1.0 | 110 | 126 | 811 | 5492 | 2850 | 26 | 28 |

Table 1 shows that the output voltage requirements are met without changing the delta count when $U_0$=1.3 V and $U_0$=2.7 V, for any values of $T_p$ and $R_l$. Accordingly, at these voltages, for the preferred embodiment there is no recalculation of delta count. However, the table shows that whenever pulse output voltage is programmed to 8.0 V, the delta count must be recalculated. The delta count is not recalculated if $R_1$ is $\geq$500 ohms and $T_p$ is $\leq$0.4 ms, because then the steep battery graph area is entered, and it is not possible to define values of RRT and LRT that safely provide a three month interval, i.e., recalculation cannot provide for specifying RRT-LRT with required accuracy.

Based on these observations, 5 separate groups of pacing conditions are identified, as follows:

1. $U_0$=1.3 V or $U_0$=2.7 V: The delta count is not recalculated.
2. $U_0$=4.0 V or $U_0$=5.3 V, $T_p \leq$0.4 ms and $R_l$=>500 Ω: The delta count is not recalculated
3. $U_0$=4.0 V or $U_0$=5.3 V, $T_p$>0.4 ms or $R_l$<500 Ω: The delta count is re-calculated to account for the longer pulse duration or the smaller load resistance.
4. $U_0$=8.0 V, $T_p$<0.4 ms and $R_l$>500 Ω: The delta count is re-calculated because the output voltage is 8.0 V.
5. $U_0$=8.0 V, $T_p$>0.4 ms or $R_l$<500 Ω: The delta count is re-calculated to account for the higher output voltage, and for the longer pulse duration or smaller load resistance.

The formulas used for recalculating the delta count are as follows:

If ($U_0$=1.3 V OR $U_0$=2.7 V), then $\Delta$cnt does not change.

If ($U_0$=8.0 V), then $\Delta$cnt=$\Delta$cnt/factor_8.

If ($R_l$<500), then: $\Delta$cnt=$\Delta$cnt {1+(1—1/factor_lead)*$R_l$/ 300–(1—1/factor_lead)*5/3}

If (0.4 ms<$T_p \leq$1.0 ms) then: $\Delta$cnt=$\Delta$cnt {1+1—1/factor_ pulse)*(1.4-$T_p$)/0.6–(1—1/factor_pulse)/0.6}

The following factors have been determined as applicable to the above equations: factor_lead=1.368; factor_pulse= 1.368; factor_8=1.825.

TABLE 2

| $U_o$ V | $T_p$ ms | $R_f$ Ω | $R_o$ Ω | $R_{no}$ Ω | Q mAh | $U_o$1 % | $U_o$2 % | $U_o$3 % | Ibat μA |
|---|---|---|---|---|---|---|---|---|---|
| 4.0 | 0.4 | 500 | 8908 | 6754 | 910 | 80 | 80 | 80 | 18.5 |
| 4.0 | 0.4 | 200 | 6512 | 4879 | 813 | 78 | 78 | 77 | 27 |
| 4.0 | 0.4 | 300 | 7310 | 5347 | 856 | 80 | 80 | 79 | 23 |
| 4.0 | 1.0 | 500 | 6512 | 4879 | 813 | 79 | 79 | 78 | 28 |
| 4.0 | 1.0 | 200 | 4760 | 2700 | 785 | 79 | 78 | 78 | 40 |
| 5.3 | 0.4 | 500 | 8908 | 6754 | 910 | 74 | 75 | 76 | 25 |
| 5.3 | 0.4 | 200 | 6512 | 4879 | 813 | 64 | 65 | 68 | 39 |
| 5.3 | 0.4 | 300 | 7310 | 5347 | 856 | 72 | 74 | 75 | 32 |
| 5.3 | 1.0 | 500 | 6512 | 4879 | 813 | 64 | 65 | 68 | 42 |
| 5.3 | 1.0 | 200 | 4760 | 2700 | 785 | 66 | 68 | 69 | 61 |
| 8.0 | 0.4 | 500 | 4880 | 2780 | 790 | 80.5 | 81 | 81 | 44 |
| 8.0 | 0.4 | 200 | 3567 | 2213 | 690 | 71 | 71 | 72 | 75 |
| 8.0 | 0.4 | 300 | 4004 | 2400 | 732 | 76 | 77 | 78 | 60 |
| 8.0 | 1.0 | 500 | 3567 | 2213 | 690 | 72 | 73 | 74 | 77 |
| 8.0 | 1.0 | 300 | 2927 | 1961 | 655 | 65 | 64 | 66 | 103 |
| 8.0 | 1.0 | 200 | 2607 | 1845 | 624 | 60 | 58 | 59 | 120 |

Table 2 shows recalculated values of $R_o$ and mAh to correspond to corrections made in accord with the above equations. This table indicates that for $U_0$=5.3 V, the requirement at standard conditions is not met. Consequently, two additional groups of pacing conditions are identified involving $U_0$=5.3 V:

6. $U_0$=5.3 V, $T_p \leq$0.4 ms and $R_l$=>500 Ω: The delta count is re-calculated because the output voltage is 5.3 V.
7. $U_0$=5.3 V, $T_p$>0.4 ms or $R_l$<500 Ω: The delta count is re-calculated to account for pulse duration, $R_l$, and also because the output voltage is 5.3 V.

In each of the two situations where $U_0$=5.3, the following formula is utilized, to account for the voltage:

If ($U_0$=5.3 V), then $\Delta$cnt=$\Delta$cnt/factor_5.3.

Factor_5.3 is determined to have a value of 1.172.

This leads to Table 3, which shows calculations for all the indicated combinations:

TABLE 3

| $U_o$ V | $T_P$ ms | $R_f$ Ω | $R_o$ Ω | $R_{no}$ Ω | Q mAh | $U_o1$ % | $U_o2$ % | $U_o3$ % | Ibat µA |
|---|---|---|---|---|---|---|---|---|---|
| 4.0 | 0.4 | 500 | 8908 | 6754 | 910 | 80 | 80 | 80 | 18.5 |
| 4.0 | 0.4 | 200 | 6512 | 4879 | 813 | 78 | 78 | 77 | 27 |
| 4.0 | 0.4 | 300 | 7310 | 5347 | 856 | 80 | 80 | 79 | 23 |
| 4.0 | 1.0 | 500 | 6512 | 4879 | 813 | 79 | 79 | 78 | 28 |
| 4.0 | 1.0 | 200 | 4760 | 2700 | 785 | 79 | 78 | 78 | 40 |
| 5.3 | 0.4 | 500 | 7600 | 5450 | 866 | 80 | 80 | 79 | 25 |
| 5.3 | 0.4 | 200 | 5555 | 4490 | 760 | 72 | 72 | 75 | 39 |
| 5.3 | 0.5 | 500 | 7260 | 5261 | 852 | 79 | 78 | 78 | 29 |
| 5.3 | 1.0 | 500 | 5555 | 4490 | 760 | 73 | 72 | 75 | 42 |
| 5.3 | 1.0 | 300 | 4558 | 3950 | 729 | 71 | 70 | 72 | 53 |
| 5.3 | 1.0 | 200 | 4061 | 3760 | 736 | 65 | 65 | 66 | 61 |
| 8.0 | 0.4 | 500 | 4880 | 2780 | 790 | 80.5 | 81 | 81 | 44 |
| 8.0 | 0.4 | 200 | 3567 | 2213 | 690 | 71 | 71 | 72 | 75 |
| 8.0 | 0.4 | 300 | 4004 | 2400 | 732 | 76 | 77 | 78 | 60 |
| 8.0 | 1.0 | 500 | 3567 | 2213 | 690 | 72 | 73 | 74 | 77 |
| 8.0 | 1.0 | 300 | 2927 | 1961 | 655 | 65 | 64 | 66 | 103 |
| 8.0 | 1.0 | 200 | 2607 | 1845 | 624 | 60 | 58 | 59 | 120 |

Based on a desire of physicians to have a follow-up time of 6 months until RRT, when the output voltage is 1.3 V or 2.7 V, the Aging factor is determined to be 1.44. Thus, the delta count divided by 1.44 yields the delta count corresponding to the impedance value at the defined Aging time, which gives the required time intervals for all combinations corresponding to output voltages of 1.3 and 2.7 V. This is summarized in Table 4:

TABLE 4

| $U_o$ V | $T_P$ ms | $R_f$ Ω | $R_o$ Ω | $R_{no}$ Ω | Q mAh | Ibat µA | Life time year | $R_o$ Ω | Q mAh | Aging time month |
|---|---|---|---|---|---|---|---|---|---|---|
| 1.3 | 0.4 | 500 | 8908 | 6754 | 910 | 11.5 | 9.04 | 6186 | 795 | 13.71 |
| 2.7 | 0.4 | 500 | 8908 | 6754 | 910 | 12.5 | 8.32 | 6186 | 795 | 12.61 |
| 4.0 | 0.4 | 500 | 8908 | 6754 | 910 | 18.5 | 5.42 | 6186 | 795 | 8.52 |
| 4.0 | 4.0 | 200 | 6512 | 4879 | 813 | 27 | 3.30 | 4522 | 668 | 7.36 |
| 4.0 | 0.4 | 300 | 7310 | 5347 | 856 | 23 | 4.09 | 5076 | 719 | 8.16 |
| 4.0 | 1.0 | 500 | 6512 | 4879 | 813 | 28 | 3.19 | 4522 | 668 | 7.10 |
| 4.0 | 1.0 | 200 | 4760 | 2700 | 785 | 40 | 2.15 | 3306 | 566 | 7.50 |
| 5.3 | 0.4 | 500 | 7600 | 5450 | 866 | 25 | 3.81 | 5278 | 735 | 7.18 |
| 5.3 | 0.4 | 200 | 5555 | 4490 | 760 | 39 | 2.13 | 3858 | 612 | 5.20 |
| 5.3 | 0.5 | 500 | 7260 | 5261 | 852 | 29 | 3.23 | 5042 | 717 | 6.38 |
| 5.3 | 1.0 | 500 | 5555 | 4490 | 760 | 42 | 1.98 | 3858 | 612 | 4.83 |
| 5.3 | 1.0 | 300 | 4558 | 3950 | 729 | 53 | 1.57 | 3165 | 645 | 2.17 |
| 5.3 | 1.0 | 200 | 4061 | 3760 | 736 | 61 | 1.38 | 2820 | 606 | 2.92 |
| 8.0 | 0.4 | 500 | 4880 | 2780 | 790 | 44 | 1.97 | 3389 | 670 | 3.74 |
| 8.0 | 0.4 | 200 | 3567 | 2213 | 690 | 75 | 1.00 | 2477 | 568 | 2.23 |
| 8.0 | 0.4 | 300 | 4004 | 2400 | 732 | 60 | 1.33 | 2781 | 602 | 2.97 |
| 8.0 | 1.0 | 500 | 3567 | 2213 | 690 | 77 | 0.98 | 2477 | 568 | 2.17 |
| 8.0 | 1.0 | 300 | 2927 | 1961 | 620 | 103 | 0.65 | 2033 | 560 | 1.26 |
| 8.0 | 1.0 | 200 | 2607 | 1845 | 588 | 120 | 0.53 | 1810 | 531 | 1.06 |

Note that in determining the respective factors such as factor_lead; factor_pulse; factor_5.3; factor_8.0 and factor_Aging, the influence of $R_{no}$ on the output pulse is taken into account. Thus, in Tables 3 and 4, $R_o$ and $R_{no}$ values are selected such that output amplitudes are within specifications.

In view of the above, there is provided a system for determining RRT, which is implemented by defining seven different groups, representing different pacing and lead conditions. It is noted that the requirement $U_0$ greater than 70% of program value is not met for the following conditions:

$U_0$=8.0 V, $T_p$=1.0 ms, $R_f$=300 Ω;

$U_0$=8.0 V, $T_p$=1.0 ms, $R_f$=200 Ω;

$U_0$=5.3 V, $T_p$=1.0 ms, $R_f$=200 Ω

The system can be expanded to recalculate the delta count so that requirements are met for these conditions. Or, to simplify, only the above seven sets of conditions are used, and the physician is advised not to program the three sets of conditions where tolerances are not met. However, this is optional, and can be utilized or not as a matter of judgment. These and other groups can be defined and used to provide even greater accuracy, but at the cost of greater complexity. It is noted that if a dual chamber pacemaker is programmed to different settings for both channels, i.e., atrium and ventricle, the worst case channel is used to calculate the delta count value. It is to be noted that when the pacemaker is programmed in a mode that consumes relatively little current, and is then reprogrammed into a more current consuming mode corresponding to which RRT has already been reached, then the pacemaker will not provide the required output amplitude. However, the safety of the patient can be guaranteed if, when the pacemaker is reprogrammed, and it is determined that the new delta count is smaller than the actual measured battery impedance, then the pacemaker is placed directly into the RRT mode, and the physician is given a warning.

Figure 4A:
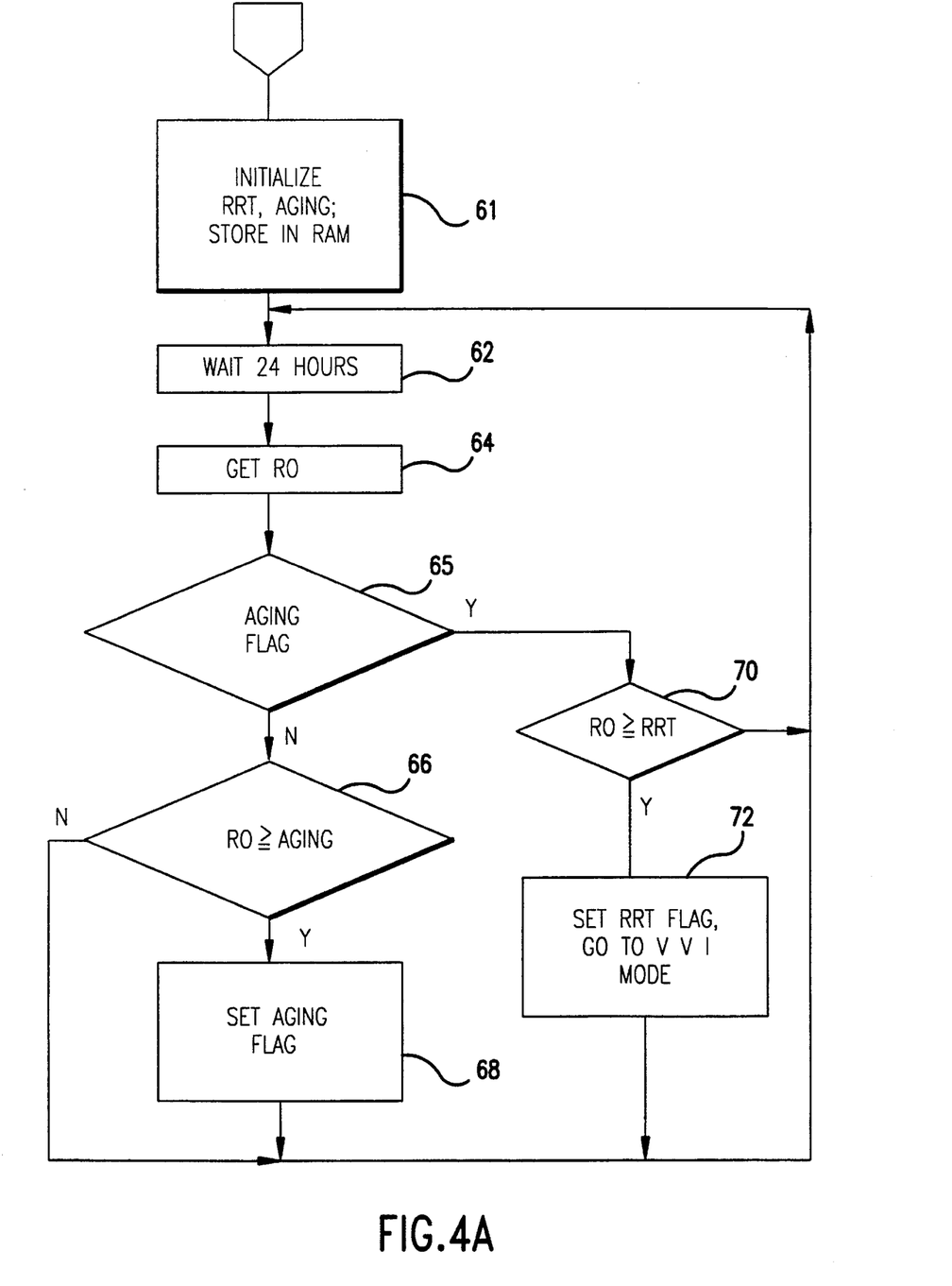
FIG. 4A is a flow diagram showing the primary steps carded out in a pacemaker in one embodiment of the system and method of this invention, for obtaining periodic measurements of battery impedance, and for responding to the condition where the pacemaker reaches Aging or RRT.

Referring now to FIG. 4A, there is shown a flow diagram of the steps taken in the pacemaker system and method of this invention, directed to comparing measured delta count, or impedance value, to the RRT value, and switching pacemaker operating conditions at RRT; and to likewise determining when Aging has been reached. At 61, at the time of production or at implant (effective BOL), the pacemaker is initialized by storing the RRT and Aging values in RAM, or other suitable memory. When the pacemaker is in use, $R_o$ is measured every 24 hours, preferably at midnight. Thus, at 62 the pacemaker is shown waiting 24 hours, and then $R_o$ is measured at 64. $R_o$ is measured by carrying out these steps: Measure $V_{bat}$ without $R_L$; Measure $V_{bat}$ loaded with $R_L$; Calculate $R_o=R_L(V_{loaded}/V_{unloaded}-1)$. At block 65, the pacemaker determines whether the Aging flag has already been set. If no, the routine proceeds to 66 and determines whether the new value of $R_o$ has reached the Aging value. If no, the routine exits; if yes, the routine goes to 68 and sets the Aging flag. It then returns to wait until the next midnight. Returning to 65, if the Aging flag has been set, then at 70 it is determined whether the measured impedance value is greater than the stored RRT value. If yes, the routine goes to 72, and sets the RRT flag; at the same time, the mode is switched, e.g., for dual chamber pacemaker operation is switched to the VVI mode. If, at 70, the impedance has not yet reached RRT, the routine exits.

Figure 4B:
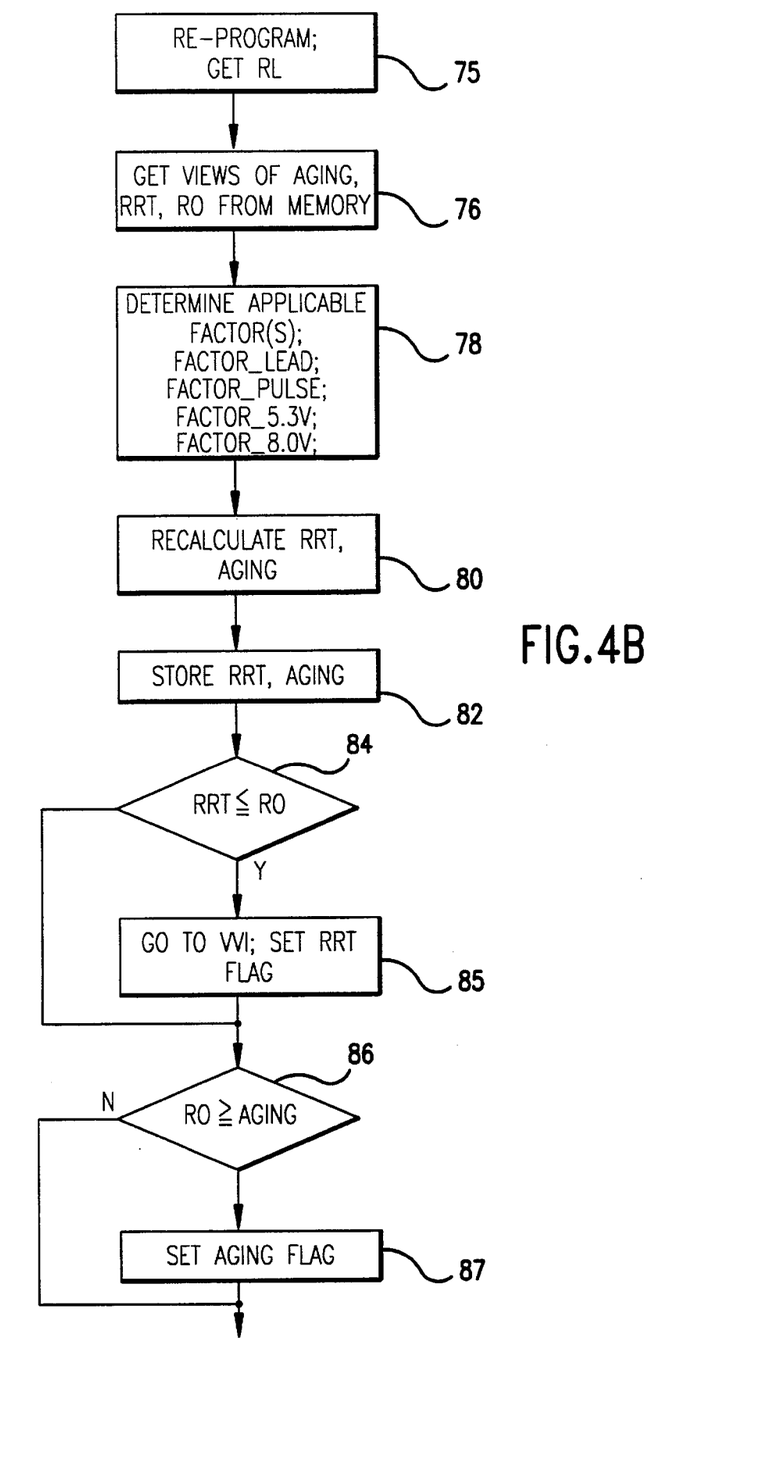
FIG. 4B is a flow diagram of the primary steps carried out in a programmer in one embodiment of this invention, for recalculating Aging or RRT in response to reprogramming of the pacemaker.

Referring now to FIG. 4B, there is shown a simplified flow diagram carried out each time the programmer is used. As indicated at block 75, the pacemaker may be reprogrammed, and/or there is a determination of load resistance. At block 76, the values of Aging, RRT, and latest measure $R_o$ are obtained from pacemaker memory. The routine then goes to block 78, and determines whether pacing conditions have been changed (i.e., change in pulse voltage or duration) or there has been a change in the lead resistance. If there has been such a change, the pacemaker finds the applicable set of circumstances, and determines which factors are to be used to recalculate the RRT and Aging values. This calculation is then performed at block 80, and the new values are stored in the pacemaker, and other external memory, at block 82. Then, at 84, the pacemaker checks to see whether the new value of RRT is less than or equal to the actual present value of $R_o$, i.e., whether actual impedance is now higher than the recalculated RRT. If yes, the routine goes to 85 and puts the pacemaker in VVI operation, and sets the RRT flag. If no, the routine skips to 86, 87 where $R_o$ is compared to the Aging value, and the Aging flag is set to warn the physician in the event that new value of Aging has now been reached.

The preferred embodiment has been described in terms of battery impedance, i.e., the $R_o$ of FIG. 2, as the battery parameter that is measured and monitored. However, the invention includes use of other battery parameters, e.g., $R_o+R_{no}$, or $V_{bat}$. And, although the use of a limited number of discrete sets of operating conditions permits simplification of the software calculations, the calculations can be performed through all ranges of the different variables that have an effect on battery current, and thus on RRT or other EOL determinations. In the preferred embodiment, the formulas set forth above are carried out. However, the invention can likewise be embodied by simply storing respective factors corresponding to different values of operating parameters, and recalculating by simply multiplying by the appropriate factor or factors.

What is claimed is:

1. A programmable implantable pacemaker, said pacemaker having a battery which provides energy to said pacemaker, said battery having at least one parameter which changes with cumulative expenditure of energy to said pacemaker, a controllable pulse generator for generating pace pulses, and programming means for programming said pacemaker to operate under a programmed set of operating conditions, said pacemaker further comprising:

measuring means for obtaining an actual measure of the actual value of said battery parameter;

means tier storing a reference measure of said battery parameter which is representative of a cumulative battery expenditure which correlates to desired pacemaker replacement at a time when said pacemaker still has at least a predetermined remaining time of operation;

calculating means for calculating said reference measure to provide a calculated value of said reference measure when said operating conditions are changed by said programming means, said calculating being a function of said changed conditions, and including determining that said calculated value corresponds to when said pacemaker still has at least said predetermined remaining time of operation, and for storing said calculated value as said reference measure: and comparison means for automatically comparing said actual measure with said reference measure and providing a replacement time indication as a function of said comparison.

2. The pacemaker as described in claim 1, wherein said battery parameter is battery ohmic impedance, and said comparison means compares said actual measure with said reference measure and provides an indication of replacement time when said actual measure reaches said reference measure.

3. The pacemaker as described in claim 2, wherein said pulse generator has means for generating said pace pulses at a programmed voltage amplitude, and wherein said calculating means recalculates said reference measure in response to a programmed change in said voltage amplitude of delivered pace pulses, so that said pace pulses are generated at at least a predetermined percentage of said programmed voltage amplitude for said predetermined remaining time of operation.

4. The pacemaker as described in claim 2, wherein said pulse generator has means for generating said pace pulses with a programmed time duration, and wherein said calculating means recalculates said reference measure in response to a programmed change in said time duration of delivered pace pulses.

5. The pacemaker as described in claim 2, comprising means for switching pacing operation conditions automatically when said actual measure reaches said reference measure.

6. The pacemaker as described in claim 2, comprising means for storing an Aging measure of battery impedance corresponding to battery expenditure at a predetermined time before said replacement time, and means for indicating when said actual measure reaches said Aging measure.

7. The pacemaker as described in claim 1, wherein said calculating means is automatically operative following any programmed change of pace pulse voltage or time duration, further having means for recalculating said reference measure in response to any programmed change in said pace pulses.

8. The pacemaker as described in claim 1, wherein said calculating means comprises stored data representing factors which correspond to a plurality of different sets of programmed pacing conditions, and said calculating means comprises recalculating means for recalculating said reference measure as a function of any programmed change that causes said pacemaker to operate with a different one of said sets of conditions.

9. A programmable pacing system, said system comprising an implantable pacemaker and a lead for transmitting generated pace pulses from said implantable pacemaker to a patient's heart, said pacemaker having a battery which provides energy to said pacemaker, said battery having at least one parameter which changes with cumulative expenditure of energy to said pacemaker, a controllable pulse generator for generating pace pulses, and programming means for programming said pacemaker to operate under a programmed set of operating conditions, said system further comprising:

measuring means for obtaining an actual measure of the actual value of said battery parameter;

means for storing a reference measure of said battery parameter which is representative of a cumulative battery expenditure which correlates to desired pacemaker replacement;

calculating means for calculating said reference measure to provide a calculated value of said reference measure when said operating conditions are changed by said programming means, said calculating being a function of said changed conditions and for storing said calculated value of said reference measure;

comparison means for automatically comparing said actual measure with said reference measure and providing a replacement time indication as a function of said comparison; and lead impedance determining means for determining the impedance of said lead, and wherein said calculating means further comprises means for calculating the reference measure as a function of said determined lead impedance.

10. A method of providing an indication concerning desired replacement time of an implantable pacemaker, said pacemaker having a battery, said method utilizing a programmer for communicating with a said pacemaker implanted in a patient, comprising:

storing in said pacemaker a representation of battery impedance corresponding to desired replacement time when said pacemaker operates at given set of pacing conditions;

using said programmer to program said pacemaker to a different set of pacing conditions;

defining a plurality of sets of pacing conditions, providing a set of formulas for recalculating said stored impedance representation, each of said formulas corresponding to at least one of the programmed sets of pacing conditions, and, in response to programming, recalculating a new value of said impedance representation in accordance with the formula corresponding to the programmed set of conditions, and storing said new value as said representation in said pacemaker;

continually obtaining a measure of actual battery impedance in said pacemaker and comparing the same with said representation; and providing an indication that desired replacement time has been reached as a function of said comparison.

11. The method as described in claim 10, comprising enabling said programmer to program said pacemaker to provide a plurality of respective pace pulse voltages, defining factors corresponding to at least certain ones of said pace pulse voltages, selecting the corresponding factor following a programmed change to one of said certain voltages, and using said factor to recalculate said impedance representation.

12. The method as described in claim 10, comprising enabling said programmer to program said pacemaker to provide a plurality of respective pace pulse time durations, defining factors corresponding to at least certain ones of said pace pulse time durations, selecting the corresponding factor following a programmed change to one of said certain time durations, and using said factor to recalculate said impedance representation.

13. The method as described in claim 10, wherein said pacemaker has a lead attached thereto for delivering pace pulses to said patient, said lead having a variable impedance, further comprising measuring said lead impedance, and recalculating said impedance representation as a function of said measured lead impedance.

14. A programmable pacing system, said system comprising an implantable pacemaker having a battery which provides energy to said pacemaker, said battery having at least one parameter which changes with cumulative expenditure of energy to said pacemaker, a controllable pulse generator for generating and delivering pace pulses, a lead for transmitting said generated pace pulses to a patient's heart, operating means for controlling said pacemaker to operate under a selected set of operating conditions, said system further comprising:

measuring means for continually obtaining a representation of the actual value of said battery parameter;

storing means for storing a reference measure of said battery parameter which has been calculated to represent the value of said battery parameter at which pacemaker replacement is desired so long as said pacemaker continually operates at the same operating conditions;

means for defining a plurality of sets of operating conditions;

recalculate means for recalculating the value of said reference measure whenever said pacemaker changes operating conditions to another one of said plurality of sets, and for storing said value as said reference measure in said storing means; and comparison means for continually comparing said actual measure with said reference measure and providing a replacement time indication as a function of said comparison.

15. The pacing system as described in claim 14, wherein said battery parameter is ohmic impedance, and said comparison means compares said actual measure with the stored reference impedance measure and provides an indication of replacement time when said actual measure is as great as or greater than said reference measure.

16. The pacing system as described in claim 15, wherein said changing means comprises programmer means for externally programming said pacemaker to operate at a different one of said first sets of operating conditions.

17. The pacing system as described in claim 16, wherein said programmer means comprises means to program said pacemaker to one of a predetermined combination of pace pulse voltages and time durations, and said recalculate means comprises stored factors for use in recalculating the value of said reference measure.

* * * * *

UNITED STATES PATENT AND TRADEMARK OFFICE
CERTIFICATE OF CORRECTION

PATENT NO. : 5,620,474
DATED : April 15, 1997
INVENTOR(S) : Jan Koopman

It is certified that error appears in the above-indentified patent and that said Letters Patent is hereby corrected as shown below:

At column 11, line 32 [claim 1, line 11], "tier" should be --for--.

Signed and Sealed this

Twenty-fifth Day of November, 1997

BRUCE LEHMAN

Attest:

Attesting Officer

Commissioner of Patents and Trademarks